US005325872A

United States Patent [19]

Westermann

[11] Patent Number: 5,325,872

[45] Date of Patent: Jul. 5, 1994

[54] TINNITUS MASKER

[75] Inventor: Søren E. Westermann, Hellerup, Denmark

[73] Assignee: Tøpholm & Westermann ApS, Vaerloese, Denmark

[21] Appl. No.: 923,803

[22] PCT Filed: Mar. 2, 1991

[86] PCT No.: PCT/EP91/00390

§ 371 Date: Aug. 31, 1992

§ 102(e) Date: Aug. 31, 1992

[87] PCT Pub. No.: WO91/17638

PCT Pub. Date: Nov. 14, 1991

[30] Foreign Application Priority Data

May 9, 1990 [DE] Fed. Rep. of Germany ....... 4014872

[51] Int. Cl.⁵ ............ A61B 5/00

[52] U.S. Cl. ............ 128/897; 128/746; 600/28

[58] Field of Search ............ 128/746, 897–898; 600/28; 607/136–137

[56] References Cited

U.S. PATENT DOCUMENTS 4,759,070 7/1988 Voroba et al. ............ 128/746 X
4,984,579 1/1991 Burgert et al. ............ 128/897 X
5,167,236 12/1992 Junker ............ 128/746

*Primary Examiner*—Angela D. Sykes
*Attorney, Agent, or Firm*—Sughrue, Mion, Zinn, Macpeak & Seas

[57] ABSTRACT

The invention relates to a tinnitus masker with one or more signal generators, a controllable amplifier (2), one or two electroacoustic transducers (3) for conversion of electrical signals into acoustic signals and a voltage source, whereby at least one of the signal generators (1) generates a continuously repeated, sinusoidal pure tone signal which slowly moves through the audio frequency range and whose cycle duration can be adjusted between 0.1 and 1000 seconds.

13 Claims, 1 Drawing Sheet

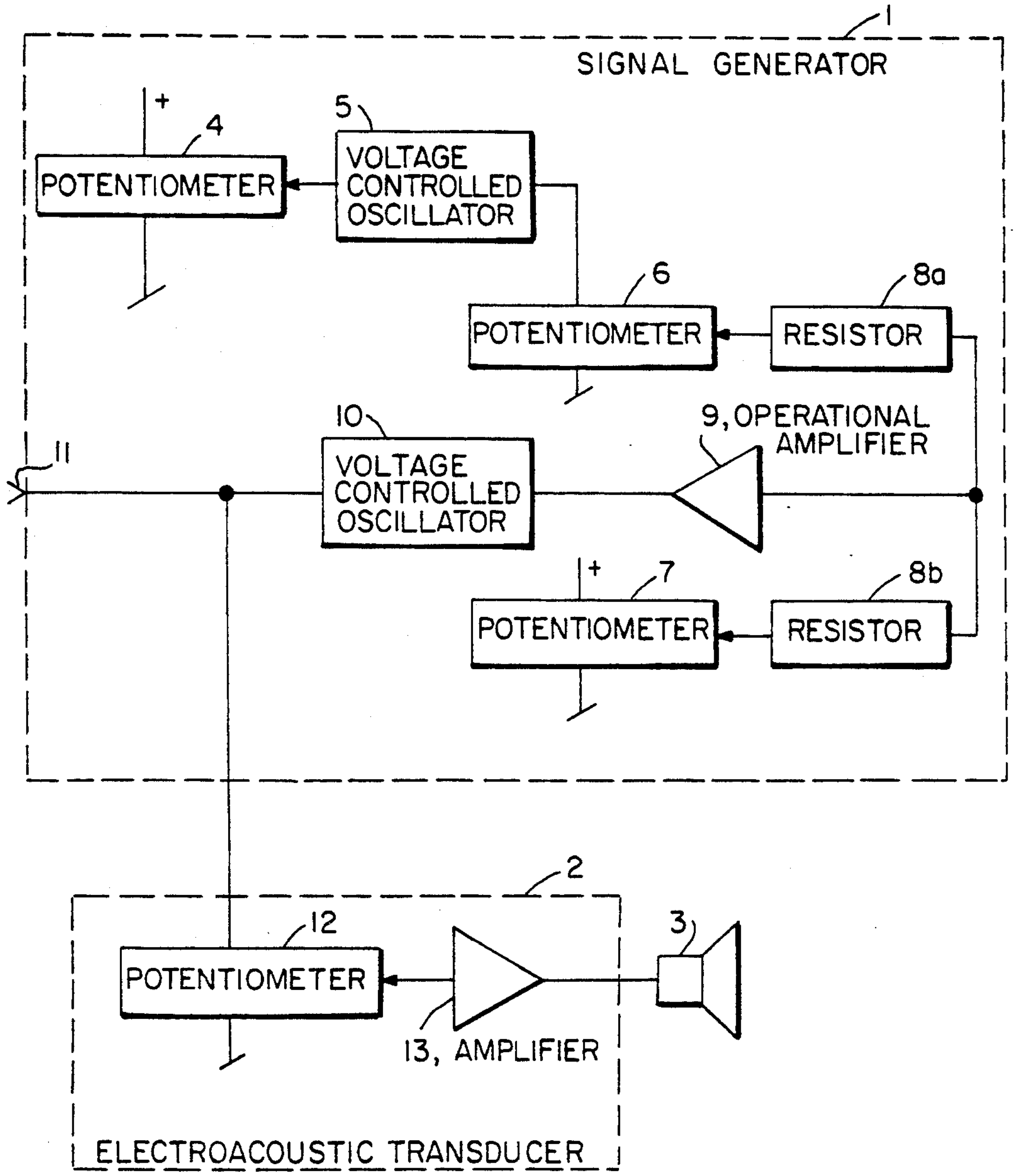
1
SIGNAL GENERATOR
+
4
5
POTENTIOMETER
VOLTAGE CONTROLLED OSCILLATOR
6
8a
POTENTIOMETER
RESISTOR
10
9, OPERATIONAL AMPLIFIER
11
VOLTAGE CONTROLLED OSCILLATOR
+
7
8b
POTENTIOMETER
RESISTOR
2
12
3
POTENTIOMETER
13, AMPLIFIER
ELECTROACOUSTIC TRANSDUCER

TINNITUS MASKER

BACKGROUND OF THE INVENTION

The invention relates to a tinnitus masker with one or more signal generators, a controllable amplifier section, one or two electroacoustic transducers for conversion of electrical signals into acoustic signals as well as a voltage source.

Such devices are already known in principle.

More than half of the world's population suffers from tinnitus in one form or the other. It is a phenomenon which occurs in the hearing system whose causes are still unclear. It may consist of anything from a weak tone which occurs only several times a year up to a continuously audible loud noise, hissing, buzzing or even a very loud tone which is never interrupted.

Tinnitus covers a wide range of phenomena which are all related to the hearing function, and particularly to the middle ear, the organ of Corti, the nerve cells and the nerve tracts as well as to the nerve centers which lead from the organ of Corti to the brain.

The actual causes of tinnitus have not yet been properly established, and it is difficult to localize them exactly.

Recent findings have shown that the nerve centers between the organ of Corti and the brain are responsible for such complex signal processing that an individual nerve cell can be located in the uppermost level of the eighth nerve of the brain which is stimulated only if a quite specific sound is identified by the nerve centers. This sound may be, for example, a quite specific phoneme or a tone with a quite specific frequency. Expressed in other words, it seems to be the task of individual or all nerve cells of this uppermost level to inform the brain that a specific sound or tone or complex tone or sound mixture has occurred. Since the human ear possesses a highly developed capability of distinguishing tones, sounds or noises of different frequencies or frequency mixtures, it is quite possible that a very large number of these nerves are intended for recognition of all those tones which belong to the audible frequency range.

This may be one of the reasons why tinnitus is very frequently perceived as a tone.

In other words, the reason why a patient believes that he is hearing a tone with a specific frequency is apparently that the nerve which would normally transmit a really audible tone of this frequency to the brain is sporadically or continuously stimulated for some reason and then remains in this stimulated condition for either a long or short period of time. This might be caused, for example, by an electromechanical fault or by such "faulty stimulation" in this or a previous nerve cell.

Earlier experiments showed that it was possible in some cases to suppress tinnitus for a certain time or even permanently be exposing the patient to various sounds and/or tones of different kinds and with different sound pressures for shorter or longer time periods. In most cases, pure sinusoidal tones were used either with high sound pressures of short duration or as so-called tinnitus maskers.

A tinnitus masker is an instrument worn on the head or on the body and on the head more or less like a hearing aid which generates a kind of acoustic signal, e.g. a sinusoidal tone, narrow-band noise, broad-band noise or white noise, which is transmitted to the patient either via an earphone or via a miniature receiver which is incorporated in a hearing aid housing. This may be a BTE device, for example.

In other cases, a standard hearing aid has been found useful, since the hearing aid boosts the overall background noise level and thus allows the patient to distinguish this from his tinnitus.

This invention relates only to such tinnitus which is perceived as a tone. In these cases, it is normally possible to identify a specific, often narrow frequency range within which the tinnitus frequency is located.

Using the above methods and techniques, even this still involved quite considerable difficulties for the patient.

If, on the other hand, a tone generator repeatedly and slowly moves through this frequency range, then it may be expected that the true tinnitus frequency is actually and repeatedly produced, although the patient does not exactly know when this is the case.

The task of the invention is thus to create a tinnitus masker of the type mentioned at the start, which appears to be particularly suitable, on the basis of tests, for treatment of the kind of tinnitus mentioned above, which makes itself noticeable by supposed hearing of a tone or tone mixture located in the audio frequency range.

The invention is based on two findings:

1. Residual suppression is recognized only if the masking signal exactly matches the tinnitus signal with respect to frequency content quality. The masking signal must be stronger.
2. Normally, it is extremely difficult for a patient to exactly assess and describe tinnitus quality.

BRIEF DESCRIPTION OF THE DRAWING

The invention will now be described in more detail on the basis of the enclosed FIGURE which shows a circuit embodiment for the signal generator used in the invention to produce the sinusoidal tone signal, whereby this circuit embodiment represents only the principle involved.

DETAILED DESCRIPTION OF THE PREFERRED EMBODIMENT

The tinnitus masker in accordance with the invention should be incorporated, for example, in a hearing aid, such as a BTE device, which contains one or more signal generators, a controllable amplifier, at least one electromechanical transducer and a voltage source.

The signal generator 1 generates a continuously repeated, sinusoidal pure tone signal which slowly moves through the audio frequency range and which is supplied to an electroacoustic transducer 3 via a controllable amplifier 2.

The tone signal generator 1 essentially consists of a voltage-controlled oscillator 5 which can be controlled via the variable output voltage of a potentiometer 4. In other words, the frequency of the signal generated by the oscillator 5 is controlled by the voltage tapped at the potentiometer 4. This signal determines the repetition frequency of the tone signal and it is typically in the range from 0.1 to 0.2 Hz. The output signal of the oscillator 5 should not contain a DC component. This output signal is supplied via a potentiometer 6 to a summing amplifier consisting of the resistors 8*a* and 8*b* and of an operational amplifier 9 and then to a second voltage-controlled oscillator 10. The summing amplifier 8*a*, 8*b*, 9 is additionally supplied by the output voltage of a further potentiometer 7. The output signal of the oscillator 10 is supplied to the output amplifier 2, which consists here, in extremely simplified form, of a potentiometer 12 and an amplifier 13, and is also supplied to a terminal 11 for a frequency counter. The electroacoustic transducer 3 is connected to the output of the amplifier 13.

The potentiometer 6 is used for adjustment of the tone frequency range covered by the tone frequency generator, while potentiometer 7 is used to set the median frequency of the covered tone frequency range.

The following procedure is followed for use of this signal generator in a tinnitus masker:

First, the potentiometer 6 is adjusted so that the output voltage of the oscillator 5 is completely attenuated. The potentiometer 7 is then used to determine an upper and lower cut-off frequency for the patient's tinnitus, i.e. the audible tone, in conjunction with an external frequency counter connected at terminal 11. The potentiometer 7 is then adjusted so that the output frequency of the oscillator 10 is located in the middle between the upper and lower cut-off frequencies. A tone signal which slowly and continuously moves through the range between the lower and upper cut-off frequencies is then generated by adjustment of potentiometers 6 and 7. The repetition frequency can be adjusted with potentiometer 4. The patient can then adjust the volume himself with potentiometer 12.

In addition, the patient can switch the noise generator of the device off or on if present.

Important is only that the repetition frequency is sufficiently low. If the repetition frequency is too high, e.g. higher than approximately 10 to 20 Hz, the tone signal is no longer perceived as a tone but as a much more complex signal which the patient no longer assigns to his tinnitus. It is thus important that the tinnitus and tone signal are perceived as equivalent.

It must be pointed out that this tinnitus masker should be used preferably only under instruction or even better under the supervision of an experienced hearing aid specialist. Even better than this would be supervision by a physician in an ENT clinic.

Of course, the circuit embodiment shown and described here represents only one of the many possibilities for design of such a tone generator, which in most cases will probably take the form of a highly-integrated circuit with a much higher number of components.

A new kind of tinnitus masker has thus been created through the invention which permits tinnitus consisting of a pure tone to be suppressed temporarily or continuously with a high probability of success.

I claim

1. In a tinnitus masker for inhibiting tinnitus comprising:

at least one signal generator (1), a controllable amplifier (2) connected to said at least one signal generator, at least one electroacoustic transducer (3) connected to said controllable amplifier for conversion of electrical signals to acoustic signals, and a voltage source, the improvement wherein said at least one signal generator (1) comprises means for generating a continuously repeated, sinusoidal pure tone signal which continuously and slowly moves through an audio frequency range in a cyclic manner to remove tinnitus for a period of time.

2. Tinnitus masker in accordance with claim 1, wherein said at least one signal generator comprises means for adjusting a cycle duration of a tone generated by a sinusoidal tone generator (10) covering the audio frequency range between 0.1 and 1000 seconds.

3. Tinnitus masker in accordance with claim 2, wherein said at least one signal generator comprises means for fixing the cycle duration of the tone generated by said sinusoidal tone generator covering said audio frequency range between 0.1 and 1000 seconds.

4. Tinnitus masker in accordance with claim 3, wherein said at least one signal generator comprises means for adjusting upper and lower cut-off frequencies of a frequency range covered by said sinusoidal tone generator (10).

5. Tinnitus masker in accordance with claim 4, wherein said at least one signal generator comprises means for adjusting a median frequency of between the upper and lower cut-off frequencies of the frequency range covered by the sinusoidal tone generator (10).

6. Tinnitus masker in accordance with claim 1, further comprising a further signal generator means for generating a noise signal for super imposition on the sinusoidal tone signal which continuously covers an audio frequency range.

7. Tinnitus masker in accordance with claim 6, further comprising means for adjusting a median frequency of the noise signal generated by said additional signal generator.

8. Tinnitus masker in accordance with claim 6, further comprising means for adjusting a lower and/or upper cut-off frequency of said noise signal generator.

9. Tinnitus masker in accordance with claim 6, further comprising means for switching on and off said signal generators individually or jointly.

10. Tinnitus masker in accordance with claim 1, further comprising a hearing aid which transmits said sinusoidal tone signal.

11. In a tinnitus masker for inhibiting tinnitus comprising:

at least one signal generator (1), a controllable amplifier (2) connected to said at least one signal generator, at least one electroacoustic transducer (3) connected to said controllable amplifier for conversion of electrical signals to acoustic signals, and a voltage source, the improvement wherein said at least one signal generator (1) comprises means for generating a continuously repeated, sinusoidal pure tone signal which continuously and slowly moves through an audio frequency range in a cyclic manner to remove tinnitus for a period of time, and wherein said controllable amplifier includes an adjustable output amplifier (13) connected to said at least one electroacoustic transducer, and wherein said at least one signal generator (1) comprises a first voltage-controlled oscillator (5) for generation of the continuously repeated, sinusoidal pure tone signal which continuously and slowly moves through the audio frequency range, means for applying an output signal of said first voltage-controlled oscillator via a first potentiometer, together with an output signal of a second potentiometer (7), to a second voltage-controlled oscillator (10) via a summing amplifier (8*a*, 8*b*, 9), an output signal of said second voltage-controlled oscillator (10) being supplied to said variable output amplifier (13) and thus to said at least one transducer (3).

12. Tinnitus masker in accordance with claim 11, wherein said at least one signal generator comprises means for controlling said first voltage-controlled oscillator (5) by an output voltage of a third potentiometer (4).

13. Tinnitus masker in accordance with claim 12, wherein said at least one signal generator means comprises a further output means (11) for a frequency counter provided at the output of said second voltage-controlled oscillator.

* * * * *